US010413728B2

(12) United States Patent
Carter et al.

(10) Patent No.: US 10,413,728 B2
(45) Date of Patent: Sep. 17, 2019

(54) ELECTROCOCHLEOGRAPHY TESTING IN HEARING PROSTHESES

(71) Applicant: Cochlear Limited, Macquarie University (AU)

(72) Inventors: Paul Michael Carter, West Pennant Hills (AU); Robert Alistair Southwood, Manly Vale (AU)

(73) Assignee: Cochlear Limited, Macquarie University, NSW (AU)

(*) Notice: Subject to any disclaimer, the term of this patent is extended or adjusted under 35 U.S.C. 154(b) by 0 days.

(21) Appl. No.: 15/488,683

(22) Filed: Apr. 17, 2017

(65) Prior Publication Data

US 2017/0304632 A1 Oct. 26, 2017

Related U.S. Application Data

(60) Provisional application No. 62/326,104, filed on Apr. 22, 2016.

(51) Int. Cl.
*A61N 1/36* (2006.01)

(52) U.S. Cl.
CPC ..... *A61N 1/36038* (2017.08); *A61N 1/36036* (2017.08); *A61N 1/36185* (2013.01)

(58) Field of Classification Search
CPC ............ A61N 1/36032; A61N 1/36185; A61N 1/36038; A61N 1/36036
See application file for complete search history.

(56) References Cited

U.S. PATENT DOCUMENTS

| | | | |
|---|---|---|---|
| 6,205,360 B1 * | 3/2001 | Carter ................ | A61N 1/36036 607/57 |
| 8,170,677 B2 * | 5/2012 | Chambers .......... | A61N 1/36032 607/55 |
| 8,364,274 B1 | 1/2013 | Litvak | |
| 2002/0026091 A1 | 2/2002 | Leysieffer | |
| 2005/0131272 A1 * | 6/2005 | Waldmann ......... | A61B 5/04845 600/25 |
| 2006/0287690 A1 * | 12/2006 | Bouchataoui ........ | H04R 25/606 607/57 |
| 2015/0289787 A1 * | 10/2015 | Buchman ............... | A61B 5/121 600/379 |
| 2016/0045749 A1 | 2/2016 | James et al. | |

FOREIGN PATENT DOCUMENTS

KR 10-2015-0117379 A 10/2015

OTHER PUBLICATIONS

International Search Report and Written Opinion of the International Searching Authority in corresponding International Application No. PCT/IB2017/052187 dated Oct. 26, 2017.

\* cited by examiner

*Primary Examiner* — Catherine Voorhees
(74) *Attorney, Agent, or Firm* — Edell, Shapiro & Finnan, LLC

(57) ABSTRACT

Presented herein are techniques for performing automated Electrocochleography (ECoG) testing using ambient sound signals received by a hearing prosthesis during normal operation (i.e., outside of a clinical setting). In particular, the hearing prosthesis analyzes ambient sound signals to identify portions of the sound signals that are conducive/suitable to the performance of an ECoG measurement (i.e., an ECoG measurement structure). When an ECoG measurement structure is identified, the hearing prosthesis itself performs an ECoG measurement using one or more implanted electrodes.

20 Claims, 8 Drawing Sheets

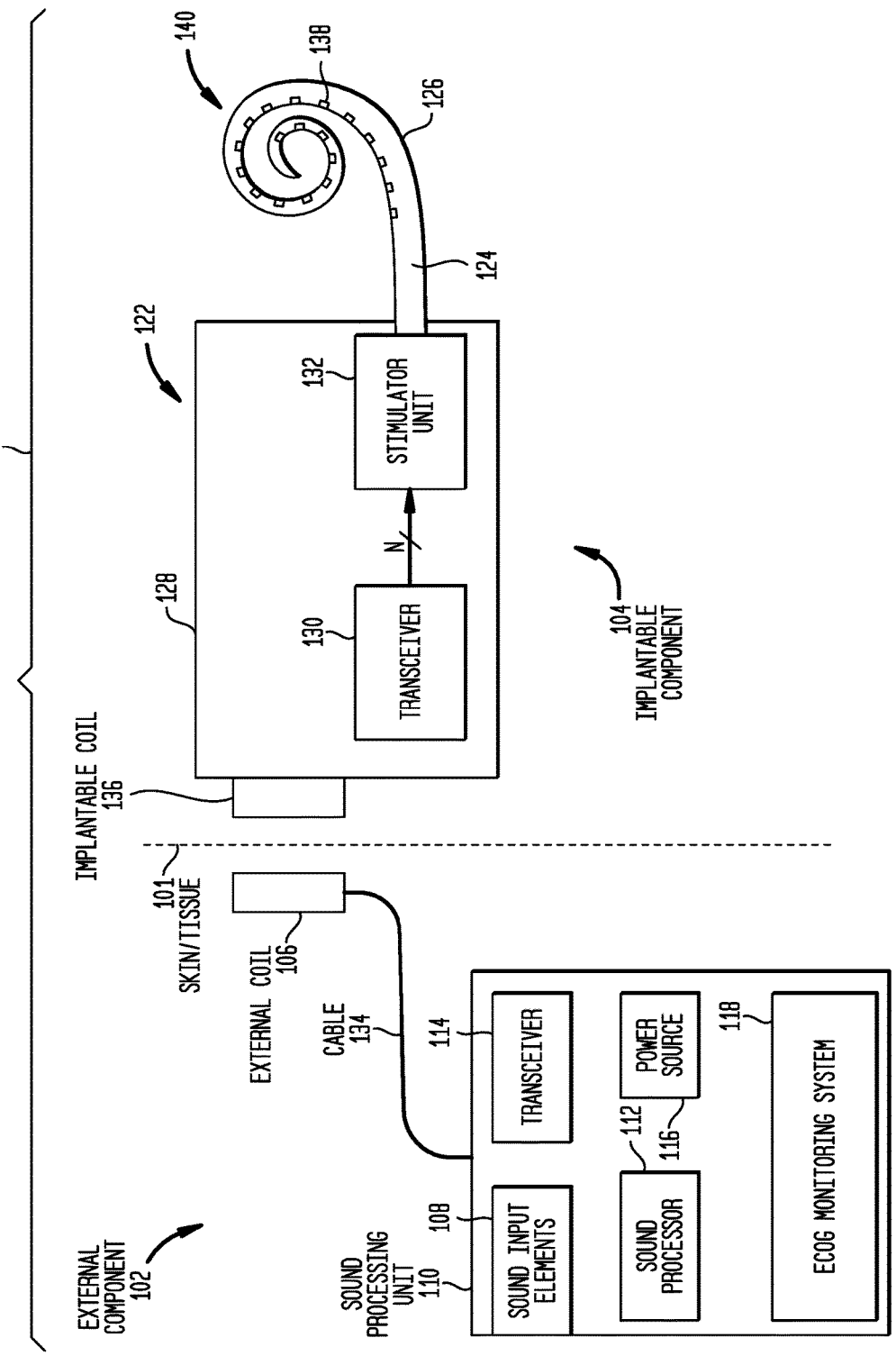

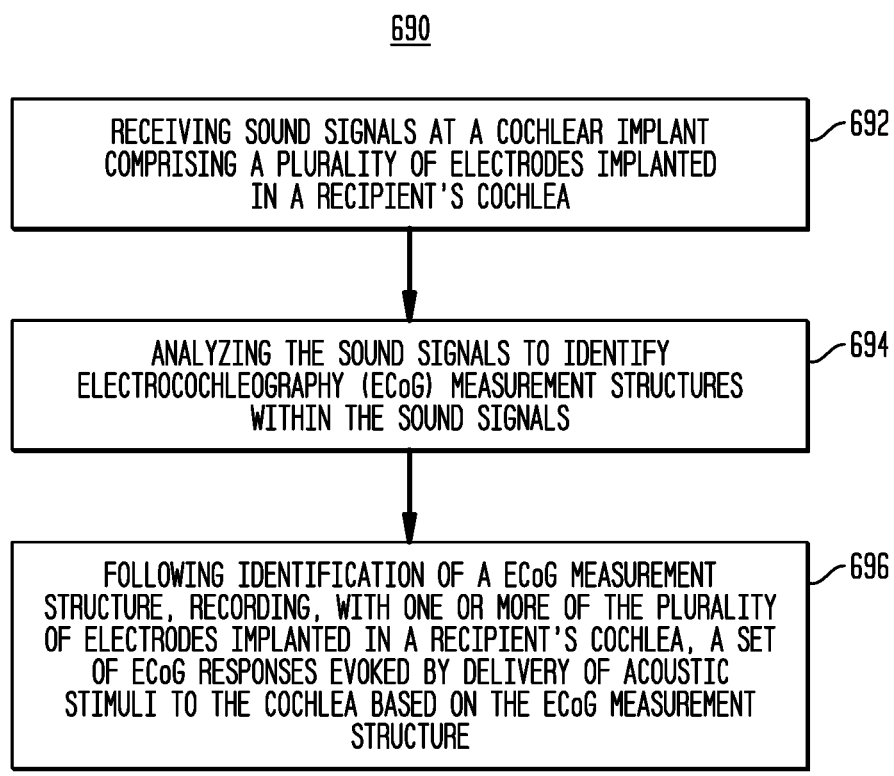

ELECTROCOCHLEOGRAPHY TESTING IN HEARING PROSTHESES

CROSS-REFERENCE TO RELATED APPLICATIONS

This application claims priority to U.S. Provisional Patent Application No. 62/326,104, filed Apr. 22, 2016, the entire contents of which is incorporated herein by reference.

BACKGROUND

Field of the Invention

The present invention relates generally to hearing prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

SUMMARY

In one aspect, a method is provided. The method comprises: receiving sound signals at a cochlear implant comprising a plurality of electrodes implanted in a recipient's cochlea; analyzing the sound signals to identify Electrocochleography (ECoG) measurement structures within the sound signals; and following identification of an ECoG measurement structure, recording, with one or more of the plurality of electrodes implanted in a recipient's cochlea, a set of ECoG responses evoked by delivery of acoustic stimuli to the cochlea based on the ECoG measurement structure.

In another aspect, a hearing prosthesis is provided. The hearing prosthesis comprises: one or more sound input elements configured to receive ambient sound, wherein a plurality of portions of the ambient sound are delivered as acoustic stimuli to a cochlea of a recipient of the hearing prosthesis; and an Electrocochleography (ECoG) monitoring system configured to record a plurality of sets of ECoG responses to the acoustic stimuli and to evaluate the residual hearing of the recipient based on the plurality of sets of ECoG responses.

BRIEF DESCRIPTION OF THE DRAWINGS

Embodiments of the present invention are described herein in conjunction with the accompanying drawings, in which:

FIG. 1B is a block diagram of the cochlear implant of FIG. 1A;

FIG. 6 is a flowchart of a method in accordance with embodiments presented herein.

DETAILED DESCRIPTION

Figure 1A:
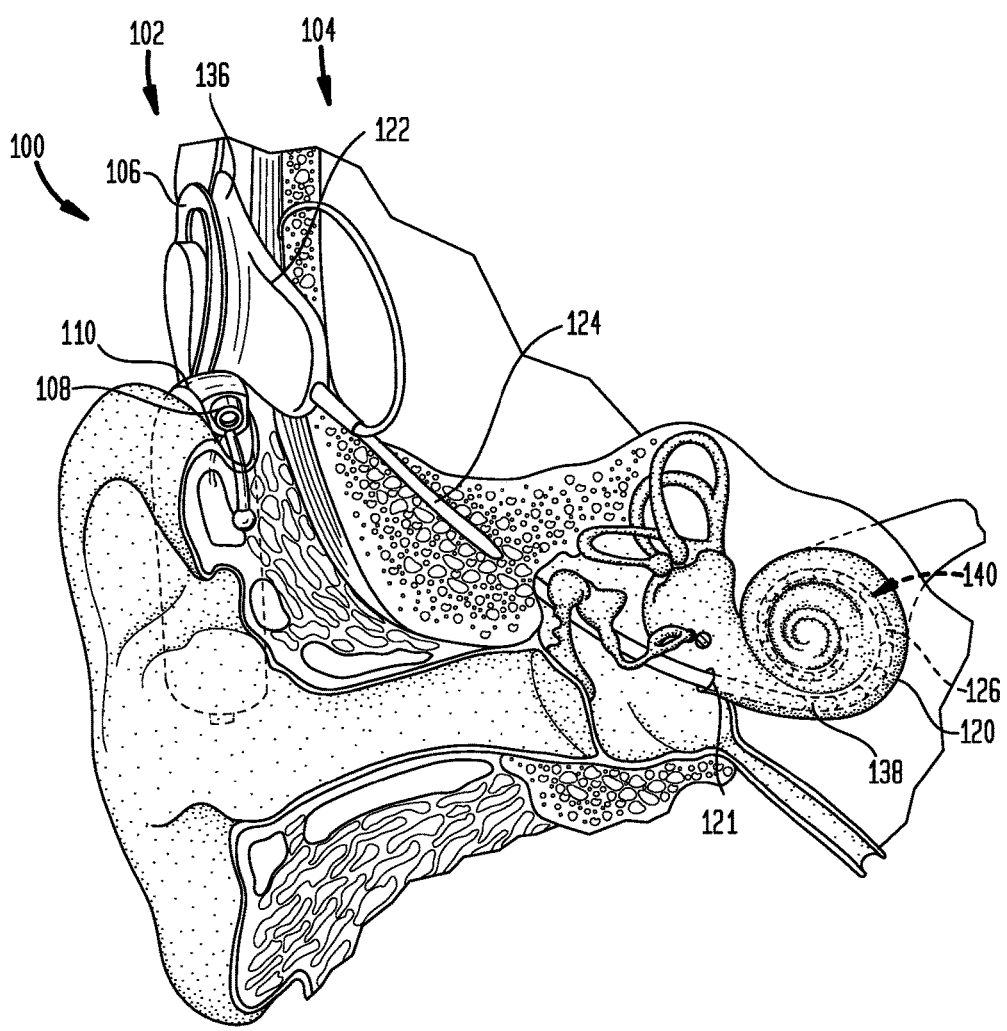
FIG. 1A is a schematic diagram illustrating a cochlear implant in accordance with embodiments presented herein.

Auditory/hearing prosthesis recipients suffer from different types of hearing loss (e.g., conductive and/or sensorineural) and/or different degrees/severity of hearing loss. However, it is now common for many hearing prosthesis recipients to retain some residual natural hearing ability (residual hearing) after receiving the hearing prosthesis. That is, hearing prosthesis recipients often retain at least some of their natural ability to hear sounds without the aid of their hearing prosthesis. For example, cochlear implants can now be implanted in manner that preserves at least some of the recipient's cochlea hair cells and the natural cochlea function, particularly in the higher frequency regions of the cochlea.

There is a risk that a recipient's residual hearing can change or deteriorate over time or in response to a sudden event, such as an infection, injury, etc. Electrocochleography (ECoG) testing is a clinical technique that can be used to assess a recipient's residual hearing. ECoG testing involves the delivery of acoustic stimuli to a recipient's cochlea, and recording one or more responses of the cochlea to the acoustic stimulus. In conventional/standard techniques, the EcoG testing is performed within a clinical environment, typically using complex equipment and techniques implemented by trained audiologists/clinicians. In particular, during conventional ECoG testing procedures, a clinician plays preselected/predetermined clicks or tones to a recipient while ECoG recordings are performed, for example, using an electrode in or near the patient's middle ear or inner ear.

Since, as noted, residual hearing can change suddenly, it would be useful to repeat a residual hearing check on a regularly basis. However, recipients often do not visit clinics on a regular basis due to, for example, costs, time constraints, low availability of trained clinicians (e.g., in rural areas), etc. Therefore, the need to visit a clinic in order to perform ECoG testing may not only be cost prohibitive for certain recipients, but cannot be reasonably undertaken on a regular basis. Accordingly, extended time periods between ECoG tests may result in a delay in detecting loss of residual hearing.

As such, presented herein are techniques that enable a hearing prosthesis itself to perform automated ECoG testing outside of a clinical setting using the normal sounds that a recipient hears in the course of their daily life (i.e., while the recipient uses the hearing prosthesis for his/her daily activity). The automated ECoG testing in accordance with embodiments presented herein can be carried out repeatedly with minimal or no involvement, or ideally even awareness, by the recipient.

In accordance with the techniques presented herein, a hearing prosthesis is configured to analyze ambient sound signals received by the hearing prosthesis during normal operation (i.e., outside of a clinical setting) to identify Electrocochleography (ECoG) measurement structures/arrangements (i.e., portions of the sound signals that are conducive/suitable to the performance of an ECoG measurement). When an ECoG measurement structure is identified, the hearing prosthesis itself performs an ECoG measurement using one or more implanted electrodes (i.e., records ECoG responses evoked by delivery of acoustic stimuli to the cochlea based on the ECoG measurement structure). The sound signal analysis and ECoG measurement can potentially be performed in a manner that is unnoticeable to most recipients. Over time, a plurality of ECoG measurements can be used to determine/detect a change in a recipient's residual hearing and possibly initiate one or more corrective actions to address the residual hearing change.

For ease of illustration, embodiments are primarily described herein with reference to one type of hearing prosthesis, namely a cochlear implant. However, it is to be appreciated that the techniques presented herein may be used with other hearing prostheses that have the ability to record ECoG responses via one or more electrodes located in or near the recipient's cochlea.

FIG. 1A is schematic diagram of an exemplary cochlear implant 100 configured to implement embodiments of the present invention, while FIG. 1B is a block diagram of the exemplary cochlear implant 100. The cochlear implant 100 comprises an external component 102 and an internal/implantable component 104.

The external component 102 is directly or indirectly attached to the body of the recipient and comprises a sound processing unit 110, an external coil 106 and, generally, a magnet (not shown in FIG. 1A) fixed relative to the external coil 106. The external coil 106 is connected to the sound processing unit 110 via a cable 134. The sound processing unit 110 comprises one or more sound input elements 108 (e.g., microphones, telecoils, etc.), a sound processor 112, an external transceiver unit (transceiver) 114, a power source 116, and an Electrocochleography (ECoG) monitoring system 118. The sound processing unit 110 may be, for example, a behind-the-ear (BTE) sound processing unit, a body-worn sound processing unit, a button sound processing unit, etc.

As shown in FIG. 1B, the implantable component 104 comprises an implant body (main module) 122, a lead region 124, and an elongate intra-cochlear stimulating assembly 126. The implant body 122 generally comprises a hermetically-sealed housing 128 in which an internal transceiver unit (transceiver) 130 and a stimulator unit 132 are disposed. The implant body 122 also includes an internal/implantable coil 136 that is generally external to the housing 128, but which is connected to the transceiver 130 via a hermetic feedthrough (not shown in FIG. 1B). Implantable coil 136 is typically a wire antenna coil comprised of multiple turns of electrically insulated single-strand or multi-strand platinum or gold wire. The electrical insulation of implantable coil 136 is provided by a flexible molding (e.g., silicone molding), which is not shown in FIG. 1B. Generally, a magnet is fixed relative to the implantable coil 136.

Elongate stimulating assembly 126 is configured to be at least partially implanted in the recipient's cochlea 120 (FIG. 1A) and includes a plurality of longitudinally spaced intra-cochlear electrical stimulating contacts (electrodes) 138 that collectively form a contact array 140. In certain arrangements, the contact array 140 may include other types of stimulating contacts, such as optical stimulating contacts, in addition to the electrodes 138.

Stimulating assembly 126 extends through an opening 121 in the cochlea (e.g., cochleostomy, the round window, etc.) and has a proximal end connected to stimulator unit 132 via lead region 124 and a hermetic feedthrough (not shown in FIG. 1B). Lead region 124 includes a plurality of conductors (wires) that electrically couple the electrodes 138 to the stimulator unit 132.

Returning to external component 102, the sound input element(s) 108 are configured to detect/receive sound signals and to generate electrical output signals therefrom. These output signals are representative of the detected sound signals. The sound processor 112 is configured to execute sound processing and coding to convert the output signals generated by the sound input element(s) 108 into coded data signals that represent electrical stimulation signals for delivery to the recipient.

The sound processor 112 provides the coded data signals to the transceiver 114, which then transcutaneously transfers the coded data signals to the cochlear implant 104 via external coil 106. More specifically, the magnets fixed relative to the external coil 106 and the implantable coil 136 facilitate the operational alignment of the external coil 106 with the implantable coil 136. This operational alignment of the coils enables the external coil 106 to transmit the coded data signals, as well as power signals received from power source 116, to the implantable coil 136. In certain examples, external coil 106 transmits the signals to implantable coil 136 via a radio frequency (RF) link. However, various other types of energy transfer, such as infrared (IR), electromagnetic, capacitive and inductive transfer, may be used to transfer the power and/or data from an external component to a cochlear implant and, as such, FIG. 1 illustrates only one example arrangement.

In general, the coded data signals received at implantable coil 136 are provided to the transceiver 130 and forwarded to the stimulator unit 132. The stimulator unit 132 is configured to utilize the coded data signals to generate stimulation signals (e.g., current signals) for delivery to the recipient's cochlea via one or of the electrodes 138. In this way, cochlear implant 100 stimulates the recipient's auditory nerve cells in a manner that causes the recipient to perceive the received sound signals by bypassing absent or defective hair cells that normally transduce acoustic vibrations into neural activity.

As noted, the sound processing unit 110 also includes an ECoG monitoring system 118 (FIG. 1B). As described further below, the ECoG monitoring system 118 is configured to perform in situ ECoG testing based on ambient sound signals. That is, the ECoG monitoring system is configured to actively monitor ambient sound to identify sound signal portions/segments that are conducive/suitable to the performance of an ECoG measurement. Sound signal portions that are conducive/suitable to the performance of an ECoG measurement are referred to herein as "ECoG measurement structures" within the sound signals. Once an ECoG measurement structure is identified within a sound signal, an ECoG measurement is triggered. Over a period of time, the ECoG monitoring system may use a plurality of ECoG measurements to identify a change in a recipient's residual hearing and possibly initiate one or more corrective actions to address the residual hearing change.

In a normal or fully functional ear, an acoustic pressure or sound wave (i.e., a sound signal) is collected by the outer ear and channeled into and through the ear canal. Disposed across the distal end of ear cannel is a tympanic membrane that vibrates in response to sound wave. This vibration is coupled to the oval window through three bones of middle ear. The middle ear bones serve to filter and amplify sound wave, causing the oval window to articulate, or vibrate, in response to vibration of tympanic membrane. This vibration sets up waves of fluid motion of the perilymph within the cochlea to active the cochlea hair cells. Activation of the hair cells causes appropriate nerve impulses to be generated and transferred through the recipient's spiral ganglion cells and auditory nerve to the brain where they are perceived as sound.

As noted above, it is common for hearing prosthesis recipient's to retain at least part of this normal hearing functionality (i.e., retain at least one residual hearing). Therefore, the cochlea of hearing prosthesis recipient can be acoustically stimulated upon delivery of a sound signal to the recipient's outer ear without the aid of the hearing prosthesis itself. In certain recipients, the normal hearing functionality may be enhanced through the use of an acoustic transducer in or near the outer ear and/or ear canal. In such recipients, the acoustic transducer is used to, for example, filter, enhance, and/or amplify a sound signal which is delivered to the cochlea via the middle ear bones and oval window, thereby creating waves of fluid motion of the perilymph within the cochlea. In other recipients, the normal hearing functionality may be enhanced through the use of a mechanical transducer that is coupled to the individual's bone (e.g., skull, jaw, etc.). In such recipients, the mechanical transducer delivers vibration to the individual's bone, and the vibration is relayed to the cochlea so as to create waves of fluid motion of the perilymph within the cochlea.

In general, an automated ECoG measurement initiated by ECoG monitoring system 118 involves the delivery of acoustic stimuli to the recipient's cochlea 120, and recording one or more responses of the cochlea 120 to the acoustic stimulus. As used herein, acoustic stimuli refer to any type of stimulation that is delivered in a manner so as to set up waves of fluid motion of the perilymph within the cochlea 120 that, in turn, activates the hair cells inside of cochlea. As such, acoustic stimuli for performance of an automated ECoG measurement in accordance with embodiments presented herein may be delivered via a recipient's normal hearing functionality, via an acoustic transducer, via a mechanical transducer, a combination thereof, etc.

Figure 2:
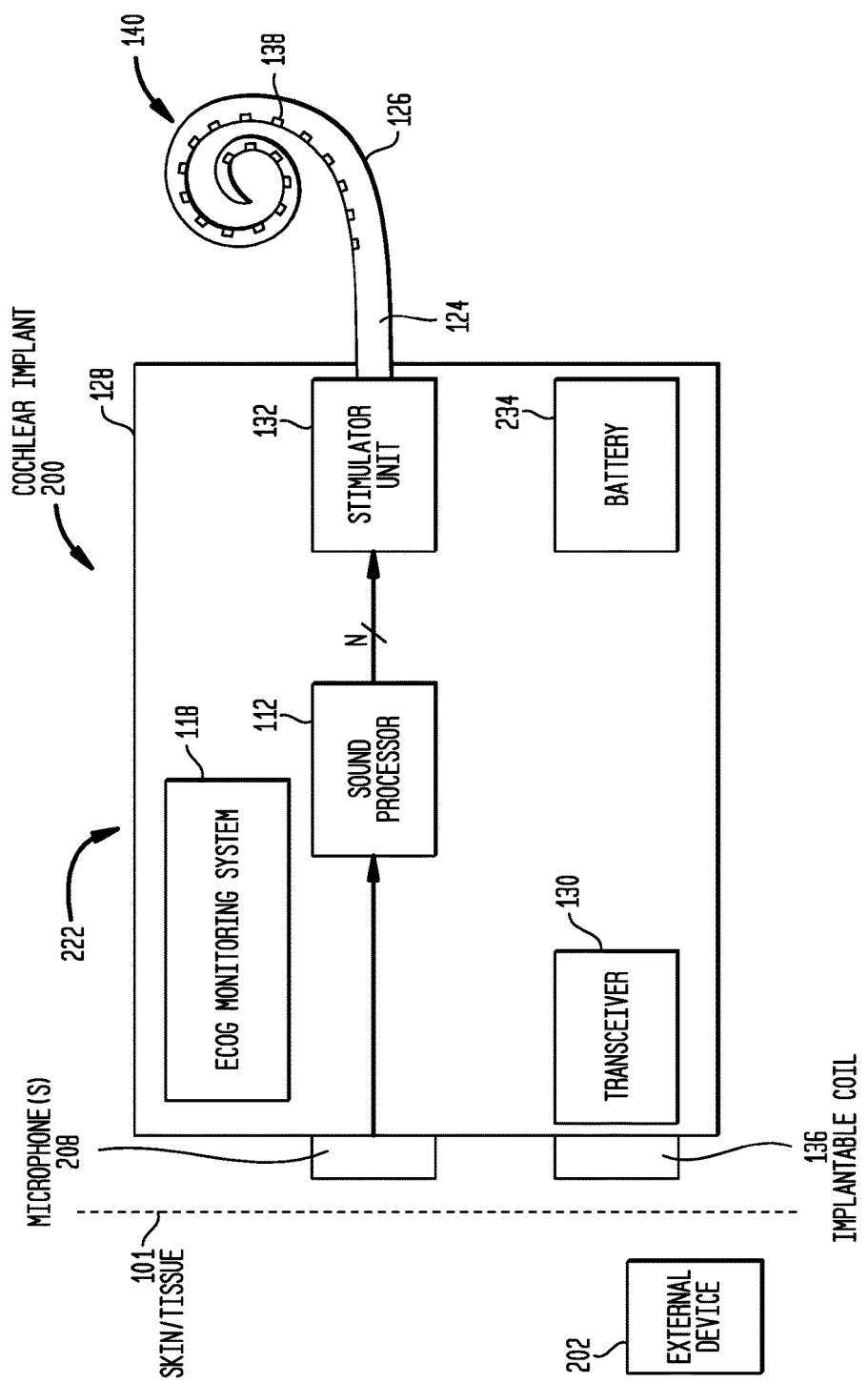
FIG. 2 is a block diagram of a totally implantable cochlear implant in accordance with embodiments presented herein.

FIGS. 1A and 1B illustrate an arrangement in which the cochlear implant 100 includes an external component 102. However, it is to be appreciated that embodiments of the present invention may be implemented in cochlear implants having alternative arrangements. For example, FIG. 2 is a functional block diagram of an exemplary totally implantable cochlear implant 200 configured to implement embodiments of the present invention. That is, in the example of FIG. 2, all components of the cochlear implant 200 are configured to be implanted under the skin/tissue 101 of the recipient. Because all components of cochlear implant 200 are implantable, cochlear implant 200 operates, for at least a finite period of time, without the need of an external device.

Cochlear implant 200 includes an implant body 222, lead region 124, and elongate intra-cochlear stimulating assembly 126. Similar to the example of FIG. 2, the implant body 222 generally comprises a hermetically-sealed housing 128 in which transceiver 130 and stimulator unit 132 are disposed. However, in the specific arrangement of FIG. 2, the implant body 222 also includes the sound processor 112, and the ECoG monitoring system 118, all of which were part of the external component 102 in FIG. 1. The implant body 222 also includes the implantable coil 136 and one or more implantable microphones 208 that are generally external to the housing 128. Similar to implantable coil 136, the implantable microphones 208 are also connected to the sound processor 112 via a hermetic feedthrough (not shown in FIG. 2). Finally, the implant body 222 comprises a battery 234.

Cochlear implant 200 includes sound input elements in the form of implantable microphones 208 that, possibly in combination with one or more external microphones (not shown in FIG. 2), are configured to detect/receive sound signals and generate electrical microphone output signals therefrom. These microphone output signals are representative of the detected sound signals. The sound processor 112 is configured execute sound processing and coding to convert the microphone output signals, and/or signals from other sound input elements (not shown in FIG. 2), into data signals. The stimulator unit 132 is configured to utilize the data signals to generate stimulation signals for delivery to the recipient's cochlea via one or stimulating contacts 138, thereby evoking perception of the sound signals detected by the microphones.

The transceiver 130 permits cochlear implant 200 to receive signals from, and/or transmit signals to, an external device 202. The external device 202 can be used to, for example, charge the battery 234. In such examples, the external device 202 may be a dedicated charger or a conventional cochlear implant sound processor. Alternatively, the external device 202 can include one or more microphones or sound input elements configured to generate data for use by the sound processor 112. External device 202 and cochlear implant 200 may be collectively referred to as forming a cochlear implant system.

The examples of FIGS. 1A, 1B, and 2 illustrate that an ECoG monitoring system in accordance embodiments of the present invention can be implemented as part of different portions of a hearing prosthesis and in hearing prostheses having different arrangements. However, merely for ease of illustration, further details of the embodiments presented herein will be described with reference to the embodiment shown in FIGS. 1A and 1B.

Figure 3A:
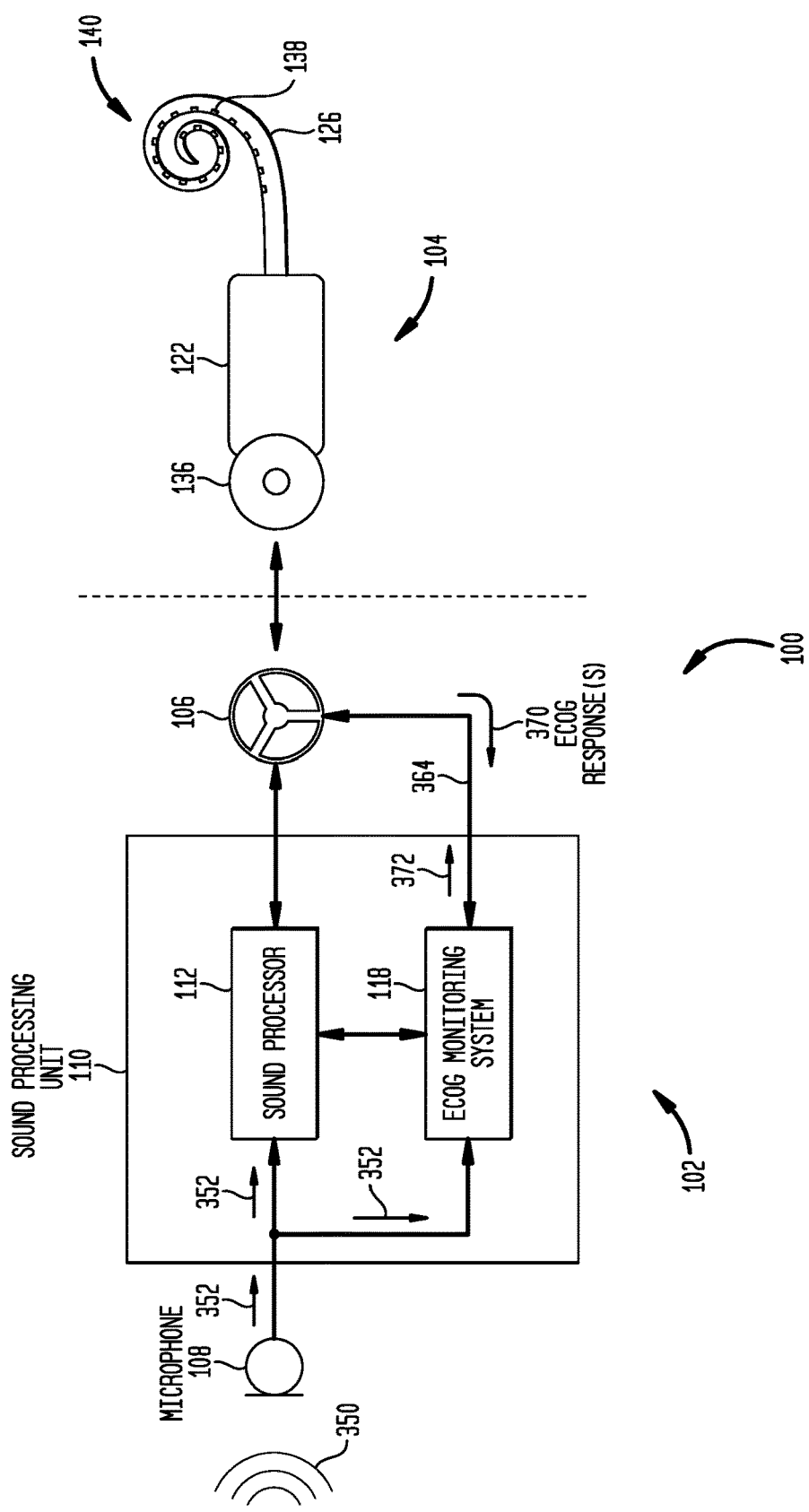
FIG. 3A is a schematic diagram illustrating integration of an ECoG monitoring system in a cochlear implant, in accordance with embodiments presented herein.
Figure 3B:
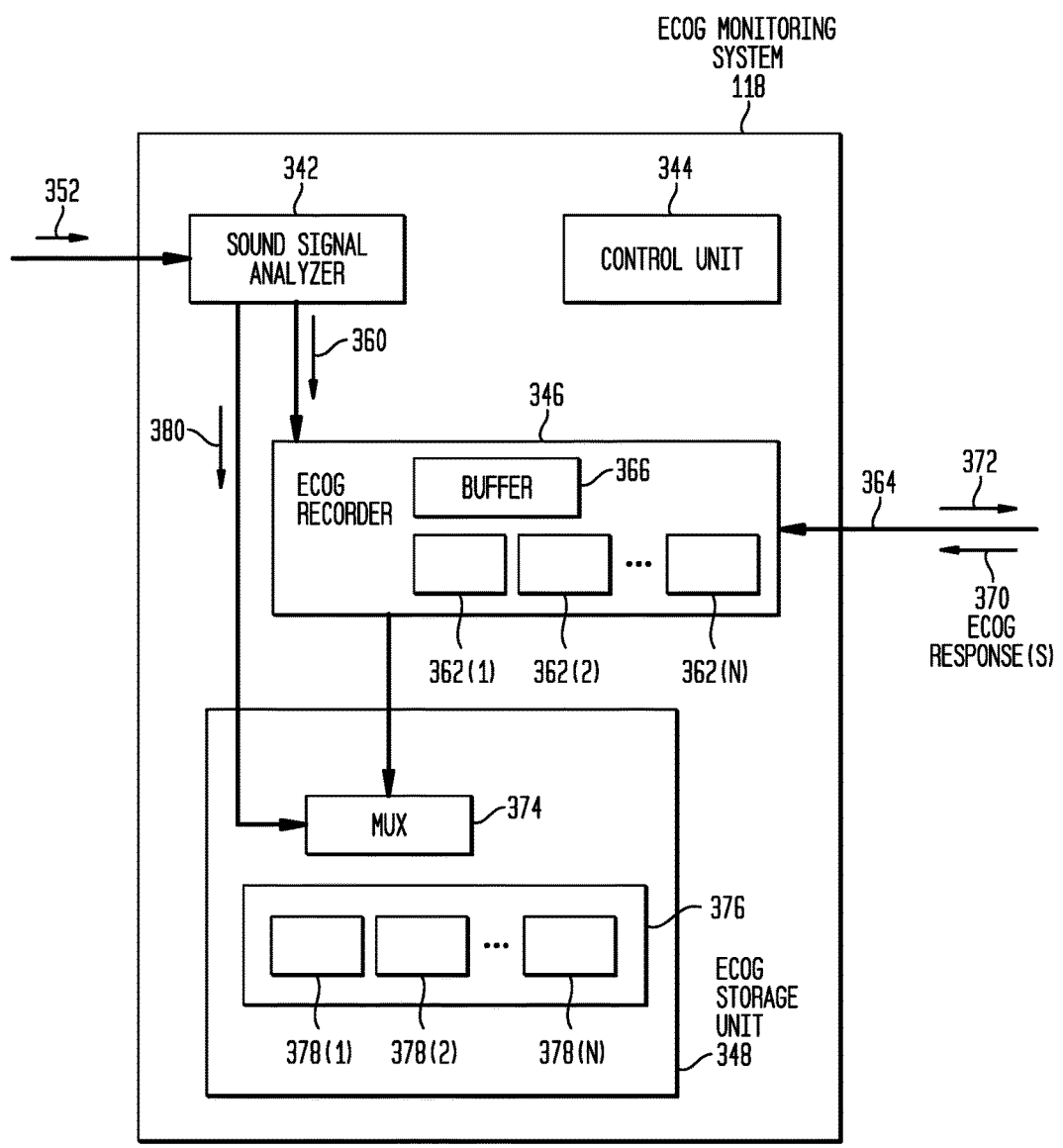
FIG. 3B is a schematic diagram illustrating further details of the ECoG monitoring system of FIG. 3A.

FIG. 3A is a schematic diagram illustrating one arrangement for integration of the ECoG monitoring system 118 in the cochlear implant 100, while FIG. 3B illustrates further details of the ECoG monitoring system 118. As shown in FIG. 3B, the ECoG monitoring system 118 includes an incoming signal analyzer (sound signal analyzer) 342, a control unit 344, an ECoG recorder 346, and an ECoG storage unit 348.

As shown in FIG. 3A, a sound input element 108 in the form of a microphone detects one or more sound signals 350 and generates one or more electrical output signals 352 therefrom. The electrical output signals 352, which are representative of the detected sound signals 350, are provided to both the sound processor 112 and the ECoG monitoring system 118. As noted, the sound processor 112 is configured to execute sound processing and coding to convert the electrical output signals 352 into coded data signals that represent electrical stimulation for delivery to the recipient.

The sound signal analyzer 342 of the ECoG monitoring system 118 is configured to analyze the electrical output signals 352 to determine whether the sound signals 350 have any ECoG measurement structures (i.e., segments/portions that are conducive/suitable to the performance of an ECoG measurement). In one example, an ECoG measurement structure is a sound portion that includes an acoustic "burst" (i.e., a sudden transition between two or more levels, such as sound pressure levels (SPLs)) with a relatively high amplitude that is proceeded by a period of quiet (i.e., a period in which the sound signal is below a predetermined level).

More specifically, speech and other common ambient sounds normally encountered by a recipient are "bursty" in nature. For example, speech consists of narrow or broad spectrum bursts, sometimes referred to as phonemes, that are interspersed/spaced by periods of relative quiet. This type of signal is well suited to performance of an ECoG measurement because the measurement can be performed following application of a burst that is preceded by a short (e.g., 10-100 millisecond (ms)) period of relative quiet.

Figure 4A:
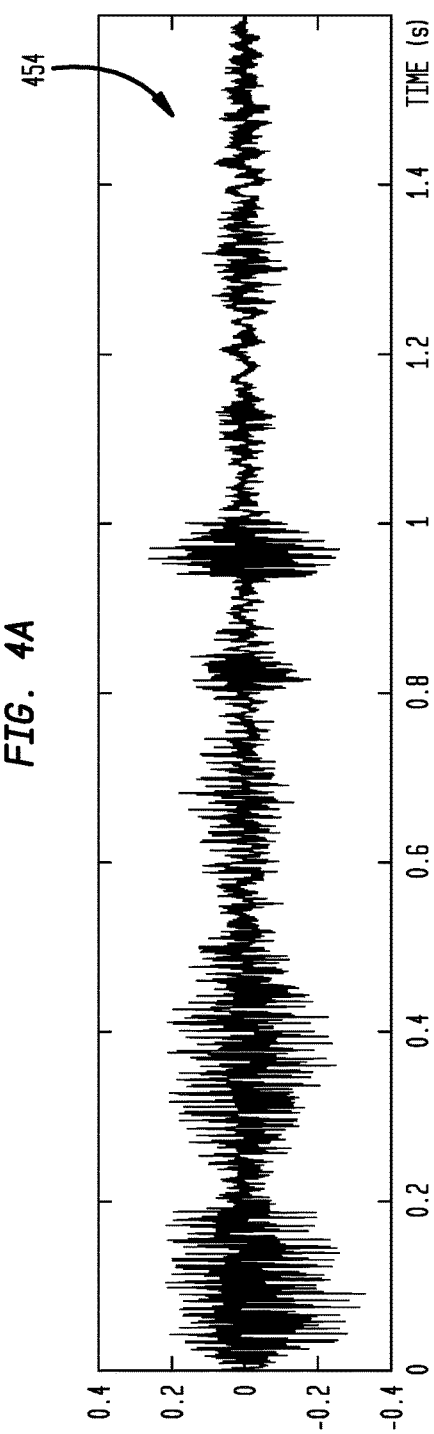
FIG. 4A is a timing diagram of an acoustic signal for analysis by an ECoG monitoring system in accordance with embodiments presented herein.
Figure 4B:
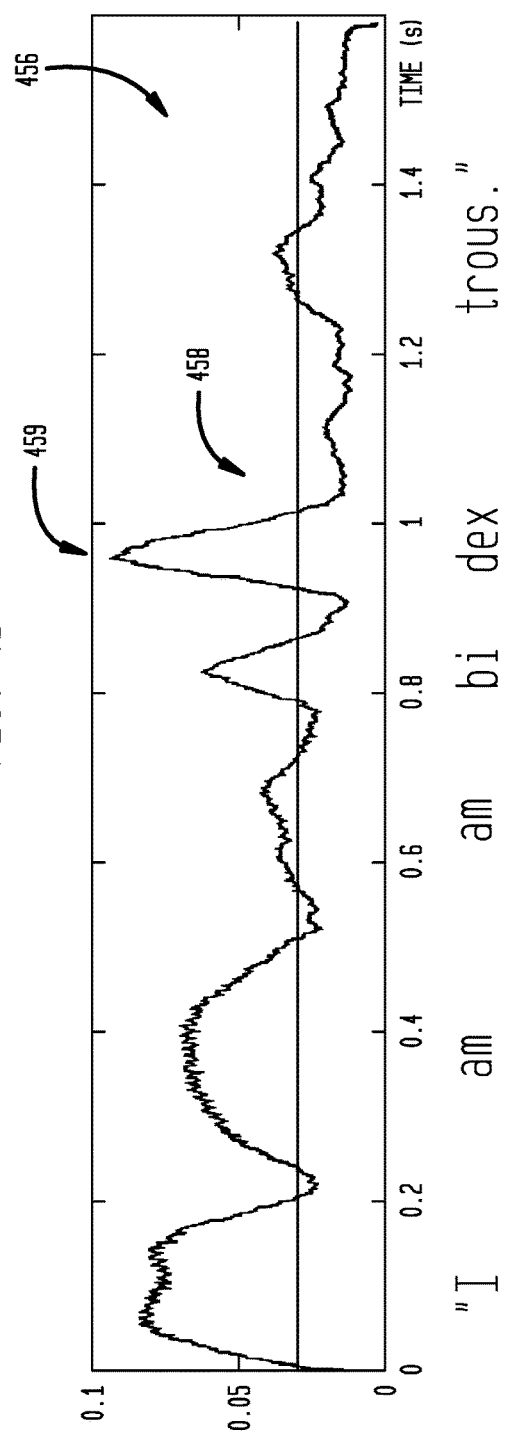
FIG. 4B is a timing diagram of the envelope of the acoustic signal of FIG. 4A.

FIG. 4A illustrates an example acoustic speech signal 454 that may be analyzed for an ECoG measurement structure, while FIG. 4B illustrates an envelope 456 generated from the speech signal 454. In this signal, a suitable opportunity to perform one ECoG measurement may be the quiet period just after (following) the phoneme "dex," which is identified in FIG. 4B by arrow 458. In this example, the phoneme "dex," which has a relatively large amplitude which lasts for roughly 50 ms (i.e., a sound burst), the proceeding relatively quiet period (i.e., the tens of ms prior to the phoneme "dex"), and the relative quiet period after the phoneme "dex" collectively comprise measurement structure 459. That is, the ECoG measurement structure 459 comprises a suitable phoneme (i.e., a portion of sufficient loudness), a period of relative before the suitable phoneme, and a period of relative quiet after the suitable phoneme.

In general, the sound signal analyzer 342 is configured to identify ECoG measurement structures as signal portions having a period of quiet preceding the onset of a sound burst. The sound burst should have a sufficient loudness to evoke the response (hair cells to react) and the preceding quiet time period should be sufficiently long so that no earlier acoustic stimuli interfere with the measurement. In certain embodiments, the burst portion of the ECoG measurement structure is be associated with a single frequency range (i.e., a narrow band burst), while in other embodiments the burst portion of the ECoG measurement structure is be associated with a plurality of frequency ranges (i.e., a broad band burst).

In further embodiments, an ECoG measurement structure has further specific timing and amplitude characteristics. For example, an ECoG measurement structure may be a signal portion having five specific sequential time periods, namely: (1) a period where the incoming sound pressure level (SPL) is less than (i.e., below) a certain threshold level (e.g., below "X" dB (SPL)) for at least a minimum period of time (e.g., for at least "A" ms); (2) a rise time that is less than a threshold period of time (i.e., less than "B" ms); (3) a period of time where the incoming SPL is greater than a threshold level (i.e., greater than "Y" dB(SPL)) for at least a minimum period of time (e.g., for at least "C" ms); (4) a decay time that is less than a threshold period of time (i.e., less than "D" ms); and (5) a final time period during which the incoming sound SPL is less than a threshold level (i.e., below "Z" dB(SPL)) for at least a minimum period of time (e.g., for at least "E" ms). In one specific example, "A," "C," and "E" may each be approximately 100 ms, "B" and "D" may each be approximately 50 ms, "X" and "Z" may each be approximately 50 dB, and "Y" may be approximately 80 dB.

In summary, an ECoG measurement structure is a portion of a sound signal received by the cochlear implant 100 which has specific timing and amplitude characteristics that are conducive to the recording of ECoG responses via one or more intra-cochlear electrodes 138. It is to be appreciated that the identification of an ECoG measurement structure means that the sound signal analyzer 342 has also determined that the corresponding sound signal portion will result in the delivery of acoustic stimuli to the recipient (i.e., will evoke a response). As described elsewhere herein, the measurement structure may or may not be perceivable by the recipient.

Returning to FIGS. 3A and 3B, the sound signal analyzer 342 continually monitors the electrical output signals 352 for ECoG measurement structures within the sound signals 350. Once an ECoG measurement structure is detected, the sound signal analyzer 342 triggers an ECoG measurement sequence. In particular, the sound signal analyzer 342 sends a message 360 to the ECoG recorder 346. Upon receipt of this message 360, the ECoG recorder 346 connects sense amplifiers 362(1)-362(N) to an input line 364 extending from external coil 106. The sense amplifiers 362(1)-362(N), when connected to input line 363, are configured to digitally record ECoG signals/responses 370 presented on the input line 364. Data recorded by the sense amplifiers 362(1)-362(N) is stored in a buffer 366.

As noted, the identification of an ECoG measurement opportunity means that the sound signal analyzer 342 has identified a sound portion that not only has specific timing and amplitude characteristics, but that will also will result in the delivery of some acoustic stimuli to the recipient via the recipient's natural hearing functionality (with or without the aid of an acoustic transducer, a mechanical transducer, etc.). The ECoG responses 370 are electrical potentials generated in the recipient's cochlea 120 when the acoustic stimuli associated with the identified ECoG measurement structure are delivered to the cochlea 120. The ECoG responses 370 are obtained by one or more of the intra-cochlea electrodes 138.

A group/set of ECoG responses 370 collected based on acoustic stimuli associated with a single ECoG measurement structure collectively comprise a single ECoG event that is recorded in the buffer 366. A single ECoG event recorded in the buffer 366 may include a plurality of different stimulus related electrical potentials (i.e., a set of ECoG responses) that comprise the cochlear microphonic (CM), the cochlear summating potential (SP), and the auditory nerve Action Potential (AP) that are measured independently or in various combinations. The cochlear microphonic is an alternating current (AC) voltage that mirrors the waveform of the acoustic stimulus at low to moderate levels of acoustic stimulation. The cochlear microphonic is generated by the outer hair cells of the organ of Corti and is dependent on the proximity of the recording electrode(s) to the stimulated hair cells. In general, the cochlear microphonic is proportional to the displacement of the basilar membrane.

The summating potential is the direct current (DC) response of the outer hair cells of the organ of Corti as they move in conjunction with the basilar membrane (i.e., reflects the time-displacement pattern of the cochlear partition in response to the stimulus envelope). The summating potential is the stimulus-related potential of the cochlea and can be seen as a DC (unidirectional) shift in the cochlear microphonic baseline. The direction of this shift (i.e., positive or negative) is dependent on a complex interaction between stimulus parameters and the location of the recording electrode(s).

The auditory nerve action potential represents the summed response of the synchronous firing of the nerve fibers in response to the acoustic stimuli, and it appears as an alternating current voltage. The auditory nerve action potential is characterized by a series of brief, predominantly negative peaks, including a first negative peak (N1) and second negative peak (N2). The auditory nerve action potential also includes a magnitude and a latency. The magnitude of the auditory nerve action potential reflects the number of fibers that are firing, while the latency of the auditory nerve action potential is measured as the time between the onset and the first negative peak (N1).

In general, the ECoG response recording may be completed within a short time period (e.g., a few milliseconds after the initial delivery of the acoustic stimuli) and does not have to wait until after completion of the acoustic stimuli. In certain embodiments, the ECoG recorder 346 can transmit a signal to the sound processor 112 and/or the stimulator unit 132 to switch the implantable component 104 from a stimulation mode/arrangement to a recording mode/arrangement. For example, prior to the recording, the ECoG recorder 346 can transmit a configuration message 372 to the implantable component 104 so that the implantable component 104 is properly configured to enable/allow recording of the ECoG responses. This message 372 may, for example, instruct the implantable component 104 (e.g., stimulator unit 132 and transceiver 132) to create a channel back to the ECoG recorder 346 over which the ECoG responses are sent.

In general, the sensitive electrical measurements required to make an ECoG recording cannot be made while the implantable component 104 is delivering stimulating to the recipient. Therefore, the implantable component 104 is switched (as a result of the configuration message 372) into the recording arrangement during the ECoG recording period and switched back into the stimulation arrangement once the recording is finished. This switching may occur during the relatively quiet periods that precede and follow an acoustic/sound burst that generates the ECoG response so that the recipient does not lose stimulation pulses during the recording period. However, it is also possible to temporarily pause/ceases electrical stimulation while the ECoG responses are recorded so as to prevent the electrical stimulation signals from swamping the recorded responses. Since the recording time period is very short (e.g., five to twenty milliseconds) the pause in electrical stimulation is short enough as to be unnoticeable to the recipient.

As noted above, the ECoG responses are recorded by one or more of the intra-cochlear electrodes 138. In certain examples, the one or more intra-cochlear electrodes 138 used for ECoG response recording may be pre-selected and used for all ECoG response recording. In other embodiments, the intra-cochlear electrodes 138 used for the ECoG response recording may change. For example, in certain embodiments, the intra-cochlear electrodes 138 used to record a set of ECoG responses are associated with the frequency of the acoustic stimuli and the burst portion of ECoG measurement structure. More specifically, because the cochlea 120 is tonotopically mapped, that is, partitioned into regions each responsive to stimulus signals in a particular frequency range, different acoustic frequencies are generally allocated to different intra-cochlear electrodes 138 based on their positioning in the cochlea 120. Accordingly, electrical stimulation signals are generally delivered via intra-cochlear electrodes 138 positioned in, or closest to, the tonotopic region most closely associated with the frequency of the sound signal portion represented by the electrical stimulation signals. This same concept may be applied to ECoG response recording where the electrode(s) 138 positioned in, or closest to, the tonotopic region most closely associated with the frequency of the acoustic stimuli are used for the resulting ECoG response recording. That is, in certain examples, ECoG measurement structures have a frequency profile that falls within a pre-programmed frequency range that will correspond to one or more intra-cochlear electrodes 138. As such, the ECoG recordings can then be taken on the corresponding intra-cochlear electrode(s), which means there is a reliable correspondence between the test signal and the measured signal. The electrode(s) 138 that are to be used for recording may be indicated in the configuration message 372 sent by the ECoG recorder 346.

A frequency map of a recipient's residual hearing may be constructed by measuring a series of ECoG recordings in response to a series of acoustic stimuli presented at a series of different frequencies. For example, ECoG recordings from acoustic signals that fall in different frequency bands (e.g. 250-500 Hz, 500-1000 Hz, etc.) could be averaged with one another. A set of ECoG responses corresponding to said frequency bands would then be available. This data would therefore provide information about the state of the recipients residual hearing at each of the frequency bands. This data may be useful, for example, to assist with remapping a recipient's acoustic frequency specific amplification level.

After a set of ECoG responses are obtained by ECoG recorder 346, the resulting ECoG response data in buffer 366 is then stored in the ECoG storage unit 348. In the example of FIG. 3B, the ECoG storage unit 348 includes a multiplexer (MUX) 374 and a memory 376. The multiplexer 374 is configured to store/average the ECoG response data into appropriate locations within memory 376. In accordance with embodiments presented herein, the memory 376 includes different locations 378(1)-378(N) into which related ECoG response data is grouped and stored. ECoG response data may be grouped/related based on one or more relational attributes. The one or more relational attributes may comprise, for example, the frequency of the triggering ECoG measurement structure (e.g., similar frequency profile groupings), burst type, amplitude and related timing characteristics, etc. Information about the type of identified acoustic signal and the characteristics of the ECoG measurement structure that caused the trigger (e.g., frequency profile) may be identified by the sound signal analyzer 342 and transferred to the multiplexer 374 so that the resulting ECoG response data is stored/averaged in the appropriate location 378(1)-378(N) (i.e., with related ECoG response data). The transfer of the acoustic signal information/characteristics from the sound signal analyzer 342 to the multiplexer 374 is shown in FIG. 3B by arrow 380. The acoustic signal information/characteristics 380 may, in certain arrangements, be stored with the corresponding ECoG response data for subsequent analysis.

The amplitude of a recorded ECoG response is typically in the microvolt range and, as such, multiple ECoG measurements (e.g., 30-100 different recording events) are performed over time and then averaged in order to reduce background noise from other sources. That is, a number of related ECoG recordings are performed and are averaged to obtain a reliable ECoG test result for the different the groupings (e.g., frequency groupings). Since, as described elsewhere herein, the ECoG recordings are performed based on ambient sound outside of the clinical environment, a plurality of ECoG recordings measurements are performed over a time and the average response (i.e., the reliable ECoG test result) may take some time to compile, depending on how frequently opportunities for ECoG recordings arise and how many measurements are desired to compute an average response.

In certain embodiments, it may be desirable to obtain ECoG responses using acoustic bursts over a range of different parameters. For example, the frequencies, amplitudes, durations, etc. of what constitutes an ECoG measurement structure may vary so as to obtain a variety of information about the hearing health of the recipient.

As noted above, the ECoG measurement system 118 includes a control unit 344. The control unit 344 is configured to set up the sense amplifiers 362(1)-362(N) as well as the recorder buffer 366. The control unit 344 also controls the multiplexer 374 to store/average the ECoG inputs into the appropriate locations. In certain examples, the control unit 344 is configured to perform analysis of the different groups of ECoG measurements. For example, after a reliable ECoG test result has been obtained, the control unit 344 may be configured to analyze the ECoG test result to determine if there has been a change in the recipient's residual hearing and, if so, to initiate one or more corrective actions. In one embodiment, the control unit 344 is configured to evaluate the residual hearing of the recipient by comparing an average of a plurality of sets of ECoG responses (i.e., a reliable ECoG test result) to a predetermined set of ECoG responses to determine if there is variance that indicates a change in the recipient's residual hearing.

There are a number of corrective actions that may be initiated when a change in the recipient's residual hearing is detected. In certain embodiments, operation of the cochlear implant 100 is adjusted based on the residual hearing change (e.g., automated device reconfiguration, such as boosting gain for certain frequencies). Other corrective actions that may be initiated upon detection of a residual hearing change include providing at least one of the recipient or a caregiver with an indication of the change, transmitting the indication of the change to a remote fitting system for analysis by an audiologist, etc. In certain arrangements, it may be possible to intervene, for instance with protective drugs, to prevent permanent residual hearing loss.

In general, the ECoG monitoring system 118 can be implemented in software and/or firmware on the cochlear implant 100. For example, the ECoG monitoring system 118 can include one or more processors configured to execute instructions stored in memory of the cochlear implant 100 to carry out the operations described above. The ECoG monitoring system 118 can also be partially or fully implemented with digital logic gates in one or more application-specific integrated circuits (ASICs).

FIGS. 3A and 3B illustrate an embodiment in which acoustic stimuli are delivered via the recipient's natural hearing. In certain embodiments, the ECoG monitoring system 118 may be included in an electro-acoustic (hybrid) hearing prosthesis that is configured to deliver both electrical stimulation signals and enhanced acoustic stimulation signals to the recipient. In such electro-acoustic hearing prostheses, the acoustic stimulation signals are delivered via an acoustic transducer. As a result, electro-acoustic hearing prostheses provide the opportunity to apply controlled acoustic stimuli to the cochlea via the acoustic transducer and then to measure the ECoG response to that signal via the intra-cochlear electrodes. In other words, electro-acoustic hearing prostheses can augment or modify the acoustic component of the delivered acoustic signal used to measure the ECoG.

Figure 5:
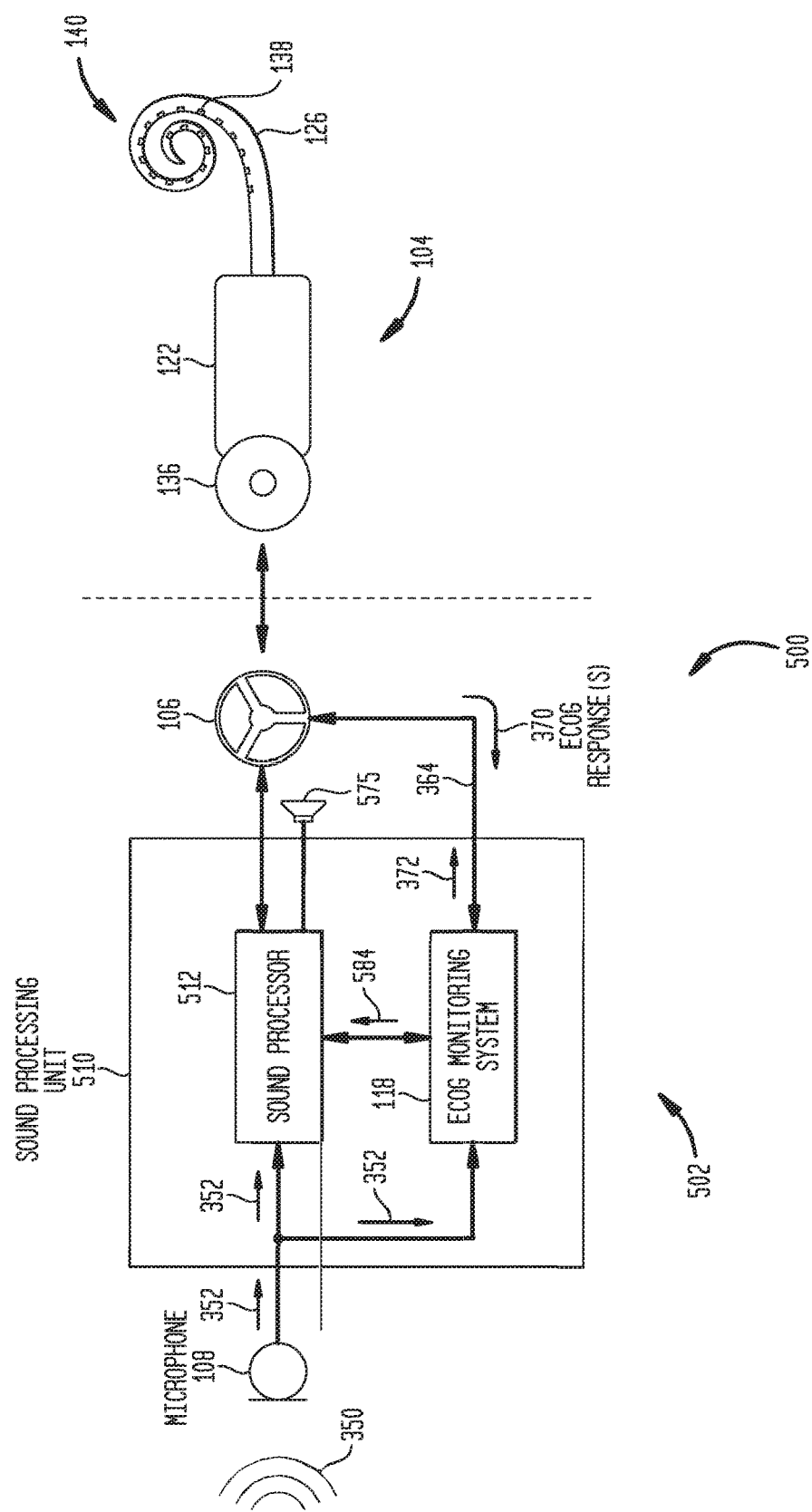
FIG. 5 is a schematic diagram illustrating integration of an ECoG monitoring system in an electro-acoustic hearing prosthesis in accordance with embodiments presented herein.

FIG. 5 is a schematic diagram of an electro-acoustic hearing prosthesis 500 that includes an embodiment of the ECoG monitoring system 118. The electro-acoustic hearing prosthesis 500 of FIG. 5 comprises an external component 502 and implantable component 104 (as described above with reference to FIGS. 1, 3A, and 3B). External component 502 includes one or more microphones 108, external coil 106, and a sound processing unit 510 that is similar to the sound processing unit 110 described above with reference to FIGS. 1, 3A, and 3B. However, in the arrangement of FIG. 5, the sound processing unit 510 includes a sound processor 512 that is configured to utilize the electrical output signals 352 to generate not only coded data signals that represent electrical stimulation for delivery to the recipient via the electrodes 138, but also coded data signals that represent acoustic stimulation for delivery to the recipient via an acoustic transducer 575.

The sound processing unit 510 also includes the ECoG monitoring system 118 described above. However, in the example of FIG. 5, the ECoG monitoring system 118 is further configured to modify the acoustic signal output by the acoustic transducer 575 to facilitate the ECoG measurement. More specifically, upon identification of an ECoG measurement structure within the sound signal 350, the ECoG monitoring system 118 is configured to issue a message 584 to the sound processor 512. Upon receipt of this message 584, the front end acoustic processing of the sound processor 512 is adjusted to modify/enhance the acoustic signal that will be delivered to the recipient via the acoustic transducer 575. In one example, the acoustic signal is adjusted so that the amplitude of an identified sound burst is increased to evoke more pronounced ECoG responses.

For example, in one such arrangement a short tone burst of controlled frequency similar to the frequency of the natural incoming sound could be delivered to the recipient via the acoustic transducer 575 at a time when a similar natural acoustic signal is detected within the environment. This modified signal is unlikely to be noticed by the recipient as it is similar to the naturally occurring signal. However, it may be a more suitable signal for use in evoking the ECoG responses since it has a precisely selected and constant frequency. In contrast, the natural signal may not be so exact or constant in its frequency. Alternatively, the electro-acoustic hearing prosthesis 500 may, for example, briefly boost the amplitude of the transmitted signal in a way that is unnoticeable to the recipient, but that enhances the response size of the ECoG. It is to be appreciated that other types of acoustic signal manipulation may be performed in accordance with embodiments presented herein in a way that is unnoticeable or minimally noticeable to the recipient so that it improves the recording of the ECoG in some way.

FIG. 6 is a flowchart of a method 690 in accordance with embodiments presented herein. Method 690 begins at 692 where a hearing prosthesis, such as a cochlear implant, receives sound signals. The hearing prosthesis includes one or more electrodes implanted in or near the recipient's cochlea. At 694, the hearing prosthesis analyzes the sound signals in order to identify Electrocochleography (ECoG) measurement structures within the sound signals. At 696, following identification of an ECoG measurement structure, the hearing prosthesis records a set of ECoG responses evoked by delivery of acoustic stimuli to the cochlea based on the ECoG measurement structure. The ECoG responses are recorded via the one or more electrodes implanted in or near the recipient's cochlea.

As noted above, presented herein are embodiments in which a hearing prosthesis is configured to perform automated ECoG testing using ambient sound signals received by the hearing prosthesis during normal operation (i.e., outside of a clinical setting). In particular, the hearing prosthesis analyzes ambient sound signals to identify portions of the sound signals that are conducive/suitable to the performance of an ECoG measurement (i.e., an ECoG measurement structure). When an ECoG measurement structure is identified, the hearing prosthesis itself performs an ECoG measurement using one or more implanted electrodes (i.e., records ECoG responses evoked by delivery of acoustic stimuli to the cochlea based on the ECoG measurement structure). The sound signal analysis and ECoG measurement can potentially be performed in a manner that is unnoticeable to most recipients. Over time, a plurality of ECoG measurements can be used to determine/detect a change in a recipient's residual hearing and possibly initiate one or more corrective actions to address the residual hearing change.

Also as noted elsewhere herein, the automated ECoG testing in accordance with the embodiments presented herein could be carried out for recipients while they are going about their daily lives, possibly in a manner unnoticeable to most recipients. The techniques presented herein improve the operation of the hearing prosthesis as it allows the prosthesis to perform automated testing and analysis that, in conventional arrangements, requires the recipient to visit a clinic. That is, the techniques presented remove the need for a recipient to go into a clinic to undergo ECoG testing to assess the recipient's residual hearing. Instead, the techniques presented herein enable the hearing prosthesis to monitor the residual hearing of a recipients so that changes to residual hearing can be detected and reacted to (e.g. with drug administration) rapidly.

As noted, embodiments of the present invention have been primarily described with reference to cochlear implants. However, it is to be appreciated that the techniques presented herein may be used with other hearing prostheses, such as auditory brainstem stimulators, direct acoustic stimulators, bone conduction devices, etc. In such arrangements, the hearing prosthesis includes at least one electrode located in or near the cochlea to perform the ECoG recording.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   receiving sound signals at a cochlear implant comprising a plurality of electrodes implanted in a recipient's cochlea, wherein each of the plurality of electrodes are electrically connected to one or more sense amplifiers;
   analyzing the sound signals to identify a plurality of Electrocochleography (ECoG) measurement structures in the sound signals; and
   recording, with one or more of the plurality of electrodes implanted in a recipient's cochlea and at least one of the one or more sense amplifiers, a plurality of sets of ECoG responses evoked by delivery of acoustic stimuli to the cochlea based on the plurality of ECoG measurement structures, wherein each set of the plurality of sets of ECoG responses corresponds to an ECoG measurement structure that is used for delivery of acoustic stimuli that evokes the corresponding set of ECoG responses.

2. The method of claim 1, further comprising:
   storing, based one or more relational attributes, at least one of the plurality of sets of ECoG responses in a memory with a plurality of previously recorded sets of ECoG responses, wherein the at least one of the plurality of sets of ECoG responses and the plurality of previously recorded sets of ECoG responses share the one or more relational attributes.

3. The method of claim 2, wherein the one or more relational attributes comprise similarities in a frequency profile of the ECoG measurement structure corresponding to the at least one of the plurality of sets of ECoG responses and frequency profiles of each of a plurality of ECoG measurement structures corresponding to the plurality of previously recorded sets of ECoG responses.

4. The method of claim 2, further comprising:
   computing an average of the at least one of the plurality of sets of ECoG responses and the plurality of previously recorded sets of ECoG responses.

5. The method of claim 4, further comprising:
   computing the average of the at least one of the plurality of sets of ECoG responses and the plurality of previously recorded sets of ECoG responses prior to storing the set of ECoG responses.

6. The method of claim 4, further comprising:
   analyzing the average of the at least one of the plurality of sets of ECoG responses and the plurality of previously recorded sets of ECoG responses relative to a predetermined set of ECoG responses to determine if there is variance indicating a change in the recipient's residual hearing.

7. The method of claim 6, wherein when there is variance, the method further comprises:
   providing at least one of the recipient or a caregiver with an indication of the variance.

8. The method of claim 6, wherein when there is variance, the method further comprises:
   adjusting operation of the cochlear implant based on the variance.

9. The method of claim 1, further comprising:
   converting the sound signals into electrical stimulation signals for delivery to the recipient via the plurality of electrodes implanted in a recipient's cochlea; and
   delaying delivery of one or more of the electrical stimulation signals until completion of the recording of one or more of the plurality of ECoG responses.

10. The method of claim 1, further comprising:
delivering the acoustic stimuli based on one or more of the plurality of ECoG measurement structures to the cochlea via an acoustic transducer.

11. A hearing prosthesis, comprising:
one or more sound input elements configured to receive ambient sound, wherein a plurality of portions of the ambient sound are delivered as acoustic stimuli to a cochlea of a recipient of the hearing prosthesis;
one or more implanted electrodes positioned at least one of in or near the cochlea; and an Electrocochleography (ECoG) monitoring system configured to:
analyze the ambient sound to identify a plurality of ECoG measurement structures within the ambient sound,
following identification of each of the plurality of ECoG measurement structures, utilize the one or more implanted electrodes to record a set of ECoG responses evoked by delivery of acoustic stimuli to the cochlea based on a respective one of the plurality of ECoG measurement structures, wherein the recordings in response to the plurality of ECoG measurement structures collectively generate a plurality of sets of ECoG responses to the acoustic stimuli,
compute an average of the plurality of sets of ECoG responses, and
evaluate the residual hearing of the recipient based on the average of the plurality of sets of ECoG response.

12. The hearing prosthesis of claim 11, wherein the ECoG monitoring system is configured to evaluate the residual hearing of the recipient by comparing the average of the plurality of sets of ECoG responses to a predetermined set of ECoG responses to determine if there is variance indicating a change in the recipient's residual hearing.

13. The hearing prosthesis of claim 12, wherein when there is variance, the hearing prosthesis is configured to provide at least one of the recipient or a caregiver with an indication of the variance.

14. The hearing prosthesis of claim 12, wherein when there is variance, the hearing prosthesis is configured to adjust operation of the cochlear implant based on the variance.

15. The hearing prosthesis of claim 11, wherein the hearing prosthesis comprises a memory, and wherein the ECoG monitoring system is configured to store each of the plurality of previously recorded sets of ECoG responses in the memory.

16. The hearing prosthesis of claim 15, wherein each of the plurality of sets of ECoG responses are stored in memory locations defined by one or more relational attributes.

17. The hearing prosthesis of claim 11, wherein the hearing prosthesis is a cochlear implant.

18. The hearing prosthesis of claim 11, further comprising:
an acoustic transducer configured to deliver the acoustic stimuli to the cochlea of the recipient.

19. A hearing prosthesis, comprising:
one or more sound input elements configured to receive sound signals, wherein a plurality of portions of the ambient sound are delivered as acoustic stimuli to a cochlea of a recipient of the hearing prosthesis;
one or more sense amplifiers;
a plurality of electrodes configured to be positioned at least one of in or near the cochlea, wherein each of the plurality of electrodes are electrically connected to at least one of the one or more sense amplifiers; and
an Electrocochleography (ECoG) monitoring system configured to:
analyze the sound signals to identify a plurality of Electrocochleography (ECoG) measurement structures in the sound signals, and
record, with one or more of the plurality of electrodes implanted in a recipient's cochlea and at least one of the one or more sense amplifiers, a plurality of sets of ECoG responses evoked by delivery of acoustic stimuli to the cochlea based on the plurality of ECoG measurement structures,
wherein each set of the plurality of sets of ECoG responses corresponds to an ECoG measurement structure that is used for delivery of acoustic stimuli that evokes the corresponding set of ECoG responses.

20. The hearing prosthesis of claim 19, wherein the ECoG monitoring system is further configured to:
store, based one or more relational attributes, at least one of the plurality of sets ECoG responses in a memory with a plurality of previously recorded sets of ECoG responses, wherein the at least one of the plurality of sets of ECoG responses and the plurality of previously recorded sets of ECoG responses share the one or more relational attributes.

* * * * *